United States Patent
Yang et al.

(10) Patent No.: US 11,497,817 B2
(45) Date of Patent: Nov. 15, 2022

(54) SENILE DEMENTIA TREATMENT FORMULATION AND APPLICATION THEREOF

(71) Applicant: MEDINTELL BIOMED, Beijing (CN)

(72) Inventors: Chenggang Yang, Beijing (CN); Feng Xiao, Beijing (CN); Changjuan Xiang, Beijing (CN)

(73) Assignee: MEDINTELL BIOMED, Beijing (CN)

( * ) Notice: Subject to any disclaimer, the term of this patent is extended or adjusted under 35 U.S.C. 154(b) by 0 days.

(21) Appl. No.: 16/770,478

(22) PCT Filed: Dec. 5, 2018

(86) PCT No.: PCT/CN2018/119432
§ 371 (c)(1),
(2) Date: Jun. 5, 2020

(87) PCT Pub. No.: WO2019/109962
PCT Pub. Date: Jun. 13, 2019

(65) Prior Publication Data
US 2021/0205474 A1  Jul. 8, 2021

(30) Foreign Application Priority Data

Dec. 6, 2017 (CN) .......................... 201711272540.5
Dec. 6, 2017 (CN) .......................... 201711272612.6
Dec. 6, 2017 (CN) .......................... 201711272650.1

(51) Int. Cl.
*C12N 15/113* (2010.01)
*A61K 48/00* (2006.01)
*A61P 25/28* (2006.01)

(52) U.S. Cl.
CPC ............ *A61K 48/005* (2013.01); *A61P 25/28* (2018.01); *C12N 15/113* (2013.01); *C12N 2310/14* (2013.01); *C12N 2310/141* (2013.01)

(58) Field of Classification Search
None
See application file for complete search history.

(56) References Cited

U.S. PATENT DOCUMENTS

2014/0377768 A1* 12/2014 Ishii ..................... C12N 15/113
435/6.13

FOREIGN PATENT DOCUMENTS

| CN | 104178418 A | 12/2014 |
| CN | 107779503 A | 3/2018 |
| CN | 107937515 A | 4/2018 |
| CN | 108034707 A | 5/2018 |
| WO | WO-2016125148 A1 | 8/2016 |

OTHER PUBLICATIONS

Fields et al. frontiers in molecular neuroscience 12, pp. 1-14 (Year: 2019).*
International Search Report (in English and Chinese) and Written Opinion of the International Searching Authority (in Chinese) issued in PCT/CN2018/119432, dated Mar. 6, 2019; ISA/CN.

* cited by examiner

*Primary Examiner* — Brian Whiteman
(74) *Attorney, Agent, or Firm* — Novick, Kim & Lee, PLLC; Allen Xue

(57) ABSTRACT

The invention relates to a diagnosis and therapeutic preparation for senile dementia and an application thereof, in particular to an application of ARHGAP11A gene, SPAG7 gene and C16ORF7 gene in preparing a diagnosis and therapeutic preparation for senile dementia. In order to solve the problem that molecular markers of senile dementia are scarce at present, the inventors carried out the high-throughput sequencing on peripheral blood samples of patients with senile dementia and healthy people, selected candidate genes, and confirmed that there was a good correlation between the candidate genes and senile dementia through molecular cell experiments, which laid a foundation for clinical gene diagnosis of senile dementia.

3 Claims, 1 Drawing Sheet

Specification includes a Sequence Listing.

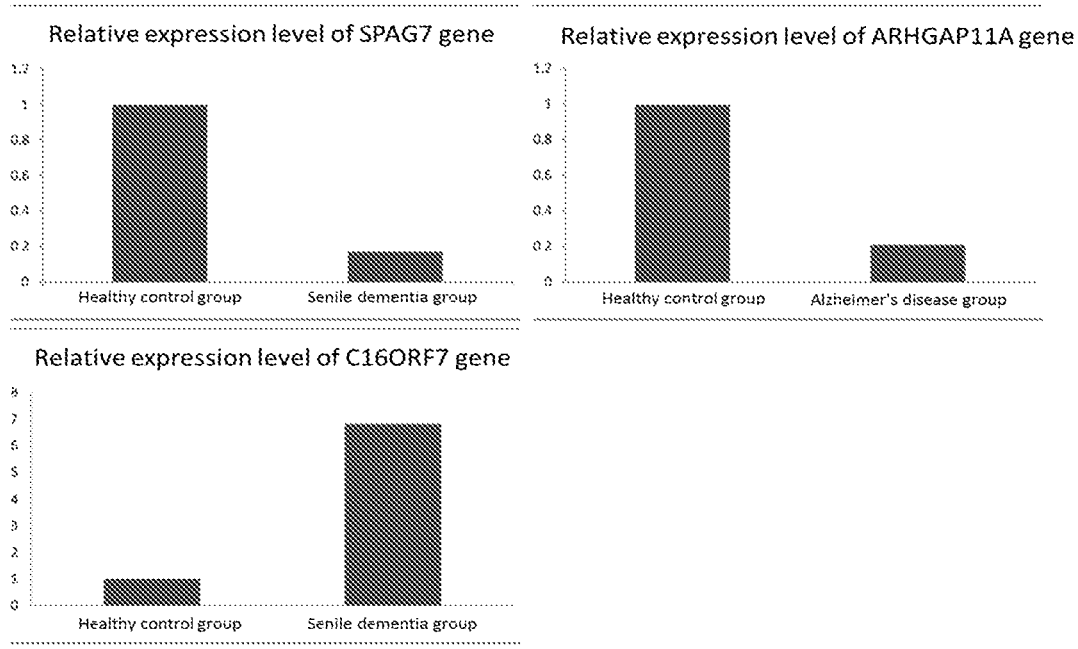

SENILE DEMENTIA TREATMENT FORMULATION AND APPLICATION THEREOF

INCORPORATION OF SEQUENCE LISTING

This application contains a sequence listing submitted in Computer Readable Form (CRF). The CFR file containing the sequence listing entitled "SequenceListing_ST25.txt", which was created on Aug. 11, 2022, and is 1,937 bytes in size. The information in the sequence listing is incorporated herein by reference in its entirety.

TECHNICAL FIELD

The invention relates to the field of biomedicine, in particular to an application of SPAG7 gene, ARHGAP11A gene and C16ORF7 gene in preparing a diagnosis and therapeutic preparation for senile dementia, in particular to an application of the gene and expression products thereof in the diagnosis and treatment of senile dementia diseases.

BACKGROUND ART

Senile dementia is also known as Alzheimer's disease (AD). The incidence of senile dementia in China is eight in every one thousand people per year. After the age of 60, the incidence and prevalence of the disease increase exponentially with the increase of age. Due to the emergence of the problem of aging population in China, the increase in the number of elderly population makes this disease one of the important factors affecting the health and life of the elderly in our country, and there is still no effective treatment for senile dementia, early diagnosis and treatment is helpful to delay the progress of the disease. Therefore, it is very important to look for biomarkers related to the diagnosis and prediction of senile dementia.

The existing methods for disease progression diagnosis include MMSE scoring test based on questionnaire, neuron imaging detection for A β amyloid protein, and some invasive methods, such as analyzing related biomolecules (A β molecule, tau protein, etc.) in cerebrospinal fluid (CSF) to help in the diagnosis of AD. Previous studies have shown that the diagnostic accuracy of AD using AD biomarkers in cerebrospinal fluid is good, but there are two obvious disadvantages: the cost is too high, which is more difficult than the biological tissue acquisition process related to peripheral blood, and the acquisition of cerebrospinal fluid causes great pain to patients and may leave sequelae. In contrast, peripheral blood is a kind of biological tissue that is easy to obtain, so it is of practical significance to study the biological changes related to AD in peripheral blood. Some molecular markers related to senile dementia have been revealed in the existing patents, such as YAP1 gene revealed by ZL2015104636167, EAPP gene revealed by ZL2015104635287, and 10 pathogenic genes related to senile dementia revealed by CN2016104739651. However, the above genes need to be further verified.

In order to solve the problem of scarcity of molecular markers of senile dementia, the inventors carried out high-throughput sequencing of peripheral blood samples from patients with senile dementia and healthy people. Bioinformatics methods were used to screen genes, and candidate genes SPAG7, ARHGAP11A and C16ORF7 were selected. Furthermore, the invention carries out RT-PCR method, cell experiment and other molecular experiments to confirm that SPAG7, ARHGAP11A and C16ORF7 have a good correlation with senile dementia, which lays a foundation for clinical gene diagnosis of senile dementia.

SUMMARY OF THE INVENTION

The invention aims to provide an application of a reagent for detecting genes and/or proteins in preparing a diagnostic preparation for neurodegenerative diseases, the genes being selected from one or more of the following genes: SPAG7, ARHGAP11A or C16ORF7.

In order to achieve the above object, the invention first selects candidate genes SPAG7, ARHGAP11A or C16ORF7 through high-throughput sequencing and bioinformatics methods, and further verifies the relationship between SPAG7, ARHGAP11A, C16ORF7 and neurodegenerative diseases through molecular cell biology methods: SPAG7, ARHGAP11A, C16ORF7 have a good correlation with neurodegenerative diseases, and can be used to prepare a therapeutic preparation for neurodegenerative diseases and/or a diagnostic preparation for neurodegenerative diseases. It has important clinical application value.

Furthermore, the diagnostic preparation of the neurodegenerative disease includes detecting the expression of SPAG7, ARHGAP11A or C16ORF7 genes in the peripheral blood of the neurodegenerative disease by fluorescence quantitative PCR method, gene chip method and sequencing method.

Fluorescence quantitative PCR is a method that uses fluorochrome or fluorescent labeled specific probe to label and trace the PCR product and monitor the reaction process on line in real time, in combination with corresponding software, to analyze the product and calculate the initial concentration of the sample template to be tested. The appearance of fluorescence quantitative PCR greatly simplifies the process of quantitative detection, and really realizes absolute quantification. The emergence of multiple detection systems makes the experiment more selective. Automatic operation improves work efficiency, which has rapid response, good repeatability, high sensitivity, strong specificity and clear results.

Gene chips, also known as DNA microarray, can be divided into three main types: 1) nucleic acid probes or cDNA fragments fixed on the surface of polymer substrates (nylon membrane, nitrocellulose membrane, etc.) are usually hybridized with isotope-labeled target genes and detected by radiography. 2) DNA probe array fixed on the glass plate by dot sampling was detected by hybridization with the fluorescence labeled target gene. 3) oligonucleotide probe array synthesized directly on the hard surface such as glass was detected by hybridization with the fluorescence labeled target gene. As an advanced, large-scale and high-throughput detection technology, gene chip is applied to diagnosis of diseases, and has the following advantages: first, it is highly sensitive and accurate; second, it is fast and simple; third, it can detect a variety of diseases at the same time. High-throughput sequencing, also known as next generation sequencing, is a revolutionary change to traditional sequencing, hundreds of thousands to millions of DNA molecules can be sequenced at a time, greatly improving sequencing efficiency. The large-scale sequencing technology greatly improves the interpretation speed of genetic information of multiple species, and provides guarantee for acquiring sequence information of all mRNAs and decrypting mRNA maps. At the same time, high-throughput sequencing makes it possible to analyze the transcriptome and genome of a species carefully and completely, so it is also called deep sequencing. Representative of high throughput sequencing platforms are Roche's 454 Sequencer (Roche GSFLX Sequencer), Illumina's Solexa Genome Analyzer, and ABI's ABI SOLiD sequencer.

The product for detecting SPAG7, ARHGAP11A or C16ORF7 genes in neurodegenerative diseases by a fluorescent quantitative PCR method contains primers for specifically amplifying SPAG7, ARHGAP11A or C16ORF7 genes; the gene chip comprises probes which hybridize with nucleic acid sequences of SPAG7, ARHGAP11A or C16ORF7 genes.

Further, the diagnostic preparation for neurodegenerative diseases comprises detecting the expression of SPAG7, ARHGAP11A or C16ORF7 protein by an immunological method. Preferably, the immunoassay method detects the expression of SPAG7, ARHGAP11A or C16ORF7 protein in neurodegenerative diseases are western blot and/or ELISA and/or colloidal gold detection method. Enzyme-linked immunosorbent assay (ELISA) is a technique in which known antigens or antibodies are adsorbed on the solid-phase carrier surface to make the enzyme-labeled antigen-antibody react on the solid-phase surface. This technique can be used to detect macromolecular antigens and specific antibodies and the like, and has the advantages of being fast, sensitive, simple and easy to standardize the carrier. The ELISA detection kit can be divided into indirect method, double-antibody sandwich method, competition method, double-site one-step method, capture method for detecting IgM antibody, and ELISA using avidin and biotin according to detection purposes and operation steps. The chromogenic substrate in the ELISA detection kit can be selected from horseradish peroxidase (HRP) or alkaline phosphatase (AP).

The commonly used immune colloidal gold detection techniques are as follows: (1) Immune colloidal gold staining method under light microscope, cell suspension smears or peripheral blood sections can be stained with colloidal gold labeled antibody, or enhanced by silver developer on the basis of colloidal gold labeling, the deposition of reduced silver atoms on the surface of labeled gold particles can significantly enhance the sensitivity of colloidal gold labeling. (2) Immune colloidal gold staining method under electron microscope, colloidal gold labeled antibodies or antiantibodies can be combined with negatively infected virus samples or ultrathin sections of peripheral blood, and then negative staining can be carried out. It can be used for virus morphology observation and virus detection. (3) Dot immuno-gold filtration method used microporous membrane as carrier to spot antigens or antibodies on the membrane, seal them and add samples to be tested. After washing, colloidal gold labeled antibodies were used to detect the corresponding antigens or antibodies. (4) Colloidal gold immunochromatography, a specific antigen or antibody is fixed on a membrane in a strip shape, a colloidal gold labeling reagent (antibody or monoclonal antibody) is adsorbed on a binding pad, when a sample to be detected is added to the sample pad at one end of a test strip, the sample moves forwards through capillary action, the colloidal gold labeling reagent on the binding pad is dissolved and then reacts with each other, and when the sample moves to an area of the fixed antigen or antibody, the conjugate of the substance to be detected and the gold standard reagent specifically binds to it and is intercepted and gathered on the detection band, and the chromogenic result can be observed with the naked eye. The method has been developed into a diagnostic test strip and is very convenient to use.

Further, the ELISA method for detecting SPAG7, ARHGAP11A or C16ORF7 proteins uses an ELISA detection kit. The antibodies in the kit can be commercially available SPAG7, ARHGAP11A or C16ORF7 monoclonal antibodies. Further, the kit comprises: a solid-phase carrier coated with SPAG7, ARHGAP11A or C16ORF7 monoclonal antibody, an enzyme-labeled secondary antibody, an enzyme substrate, a protein standard, a negative control, a diluent, a washing solution, an enzyme reaction stops solution and the like.

Further, the colloidal gold method for detecting SPAG7, ARHGAP11A or C16ORF7 protein uses a detection kit, and the antibody can be a commercially available SPAG7, ARHGAP11A or C16ORF7 monoclonal antibody. Furthermore, the colloidal gold detection kit adopts a colloidal gold immunochromatography technology or a colloidal gold filtration method. Furthermore, a detection region (T) on the nitrocellulose membrane of the colloidal gold detection kit is sprayed with anti-SPAG7, ARHGAP11A or C16ORF7 monoclonal antibodies, and a quality control region (C) is sprayed with immunoglobulin IgG.

The invention aims to provide a fluorescent quantitative PCR kit for detecting neurodegenerative diseases, which is characterized in that the kit is used for detecting genes SPAG7, ARHGAP11A or C16ORF7, and specific forward primer and reverse primer are adopted.

Furthermore, the PCR kit is suitable for all types of fluorescence quantitative gene amplifiers in the market, with high sensitivity, rapid and accurate quantification, good stability, and a good application prospect.

Further, the fluorescent quantitative PCR kit comprises the following components: specific primer, internal reference primer and fluorescent quantitative PCR reaction solution. Wherein, the specific primers comprise a forward primer and a reverse primer, the forward primer sequence is SEQ ID NO. 1, and the reverse primer sequence is SEQ ID NO. 2. The internal reference primer is a β-actin internal reference primer.

The kit further comprises an RNA extraction reagent. Preferably, TRIzol® Reagent is used for sample RNA extraction.

The sensitivity of the kit is also detected, and the result shows that the detection range of the kit is $10^6$-$10^2$ copies/μl, and the minimum detection concentration is 100 copies/μl.

The invention aims to provide a neurodegenerative disease detection kit which detects SPAG7, ARHGAP11A or C16ORF7 protein. Furthermore, the kit further comprises other detection reagents. The invention aims to provide a gene chip for detecting neurodegenerative diseases, which comprises a probe hybridized with nucleic acid sequences of SPAG7, ARHGAP11A or C16ORF7 genes.

The invention aims to provide an application of SPAG7, ARHGAP11A or C16ORF7 genes and/or proteins in preparing a therapeutic preparation for neurodegenerative diseases.

Further, the therapeutic preparation for neurodegenerative diseases refers to a preparation that can promote the expression of SPAG7 or ARHGAP11A gene. It is well known to those skilled in the art that one or more of the following methods can generally be used to promote gene expression: regulating SPAG7 or ARHGAP11A gene by DNA level: including but not limited to increasing the copies of the SPAG7 or ARHGAP11A gene, transfecting an overexpression vector containing the SPAG7 or ARHGAP11A gene; regulating SPAG7 or ARHGAP11A gene by transcription level: including but not limited to activating the expression of the SPAG7 or ARHGAP11A gene, activating a promoter that regulates the expression of the SPAG7 or ARHGAP11A gene, inhibiting a transcription factor that negatively regulates the expression of the SPAG7 or ARHGAP11A gene, and interfering an suppressor that inhibits the expression of the SPAG7 or ARHGAP11A gene by using an RNA interference technology; regulating SPAG7 or ARHGAP11A gene by post-transcriptional levels: including but not limited to inhibiting transcription expression of microRNA that promotes mRNA degradation of SPAG7 or ARHGAP11A gene, introducing microRNA that promotes SPAG7 or ARHGAP11A gene expression; regulating SPAG7 or ARHGAP11A gene by post-translational levels: including but not limited to introducing molecules that promote the proteins encoded by SPAG7 or ARHGAP11A genes, inhibiting proteins that negatively regulate the expression of SPAG7 or ARHGAP11A genes, and promoting the expression of factors and proteins that promote the expression of SPAG7 or ARHGAP11A genes.

The present invention aims to provide a preparation for treating neurodegenerative diseases, which promotes the expression of SPAG7 or ARHGAP11A gene in a patient with a neurodegenerative disease. Further, the preparation for treating neurodegenerative diseases comprises a vector for promoting SPAG7 or ARHGAP11A gene expression.

Further, the Alzheimer's therapeutic preparation refers to a preparation that inhibits the expression of the C16ORF7 gene. It is well known to those skilled in the art that one or more of the following methods can generally be used to inhibit gene expression: including but not limited to by activating the suppressor gene of the target gene, activating the protein expressed by the suppressor gene of the target gene, inhibiting the expression of the target gene by RNA interference technique, activating the microRNA that promotes the degradation of the target gene mRNA, introducing molecules that promote the degradation of the protein encoded by the target gene, and inhibiting the expression of factors and proteins that promote the expression of the target gene. That is, by activating suppressor genes of C16ORF7 gene, activating proteins that inhibit C16ORF7 gene expression, introducing siRNA that inhibits C16ORF7 gene expression, activating microRNA that promotes C16ORF7 mRNA degradation, introducing molecules that promote C16ORF7 protein degradation, and inhibiting the expression of factors and proteins that promote C16ORF7 gene expression.

RNA interference (RNAi) refers to the phenomenon that exogenous and endogenous double-stranded RNA induce specific mRNA degradation of homologous target genes in vivo, resulting in post-transcriptional gene silencing. It is a technique that uses small double-stranded RNA to efficiently and specifically block the expression of a specific gene in the body, promote mRNA degradation, and make cells show a specific gene deletion phenotype. After the design of siRNA, direct synthesis or construction of siRNA expression vector can be used. The prepared siRNA can be transfected into cells by calcium phosphate coprecipitation method, electroporation method, DEAE-dextran and polybrene method, microinjection or mechanical method like genegun, cationic liposome reagent method and so on.

Neurodegenerative diseases are Alzheimer's disease, Parkinson's disease or vascular dementia.

An application of ARHGAP11A, SPAG7 or C16ORF7 gene and/or protein in preparing a α-Syn protein regulator.

Further, promote the expression of ARHGAP11A or SPAG7 gene and/or protein, or inhibit the expression of C16ORF7 gene and/or protein to reduce the expression of α-Syn protein.

A therapeutic preparation for treating neurodegenerative diseases, which promotes the expression of ARHGAP11A or SPAG7 gene and/or protein or inhibits the expression of C16ORF7 gene and/or protein.

The preparation for treating neurodegenerative diseases comprises a vector for promoting ARHGAP11A or SPAG7 gene expression, or an interference RNA for silencing C16ORF7 gene. A method for detecting the risk of a neurodegenerative disease, comprising the steps of:

1) taking a peripheral blood sample;

2) detecting the expression level of ARHGAP11A, SPAG7 or C16ORF7 genes and/or proteins in the sample;

3) determining samples with low expression of ARHGAP11A, SPAG7 gene or protein to be at risk for neurodegenerative disease, and determining samples with high expression of C16ORF7 gene and/or protein to be at risk for neurodegenerative disease.

A method of treating the risk of a neurodegenerative disease by up-regulating the expression of ARHGAP11A, SPAG7 gene or protein or reducing the expression of C16ORF7 gene or protein in a patient.

Further, expression of the ARHGAP11A or SPAG7 gene or protein is upregulated using one and/or more of the following methods: including but not limited to increasing the copies of the SPAG7 or ARHGAP11A gene, transfecting an overexpression vector containing the SPAG7 or ARHGAP11A gene; regulating SPAG7 or ARHGAP11A gene by transcription level: including but not limited to activating the expression of the SPAG7 or ARHGAP11A gene, activating a promoter that regulates the expression of the SPAG7 or ARHGAP11A gene, inhibiting a transcription factor that negatively regulates the expression of the SPAG7 or ARHGAP11A gene, and interfering an suppressor that inhibits the expression of the SPAG7 or ARHGAP11A gene by using an RNA interference technology; regulating SPAG7 or ARHGAP11A gene by post-transcriptional levels: including but not limited to inhibiting transcription expression of microRNA that promotes mRNA degradation of SPAG7 or ARHGAP11A gene, introducing microRNA that promotes SPAG7 or ARHGAP11A gene expression; regulating SPAG7 or ARHGAP11A gene by post-translational levels: including but not limited to introducing molecules that promote the proteins encoded by SPAG7 or ARHGAP11A genes, inhibiting proteins that negatively regulate the expression of SPAG7 or ARHGAP11A genes, and promoting the expression of factors and proteins that promote the expression of SPAG7 or ARHGAP11A genes;

Further, the expression of the C16ORF7 gene or protein is reduced by one and/or more of the following methods: including but not limited to by activating the suppressor gene of the target gene, activating the protein expressed by the suppressor gene of the target gene, inhibiting the expression of the target gene by RNA interference technique, activating the microRNA that promotes the degradation of the target gene mRNA, introducing molecules that promote the degradation of the protein encoded by the target gene, and inhibiting the expression of factors and proteins that promote the expression of the target gene. That is, by activating suppressor genes of C16ORF7 gene, activating proteins that inhibit C16ORF7 gene expression, introducing siRNA that inhibits C16ORF7 gene expression, activating microRNA that promotes C16ORF7 mRNA degradation, introducing molecules that promote C16ORF7 protein degradation, and inhibiting the expression of factors and proteins that promote C16ORF7 gene expression.

BRIEF DESCRIPTION OF THE DRAWINGS

FIG. 1 is a graph showing the relative expression level of SPAG7, ARHGAP11A or C16ORF7 gene in peripheral blood of patients with senile dementia and peripheral blood of healthy people

DETAILED DESCRIPTION OF THE INVENTION

The invention is further illustrated by the following specific examples, which are intended to be illustrative only and are not to be construed as limiting the invention. One of ordinary skill in the art will appreciate that: various changes, modifications, substitutions and alterations can be made to these embodiments without departing from the principles and spirit of the invention, the scope of the invention is defined in the claims and their equivalents. Experimental procedures in which specific conditions are not indicated in the following examples are generally carried out under conventional conditions or under conditions recommended by the manufacturer.

Example 1 High Throughput Sequencing and Analysis

The samples were collected from Peking Union Medical College Hospital and the informed consent of the subjects was obtained. The peripheral blood samples of 15 patients with senile dementia and 9 healthy controls were collected for RNA extraction and agarose gel electrophoresis was carried out after RNA extraction. From the electrophoresis results, we can preliminarily determine whether the extracted RNA samples are qualified or not, and whether they can be used for further transcriptome analysis. Furthermore, the extraction condition of the RNA sample was detected through a NanoDrop 1000 spectrophotometer, and the sample requirements of RNA-seq sequencing were as follows: OD260/OD280 was 1.8-2.2.

The sequencing platform is Illumina's HiSeq 2500 high-throughput sequencing platform, which carried out high-throughput transcriptome deep sequencing. After sequencing, we used Fast-QC software to evaluate the overall quality of the sequencing data, including base quality value distribution, quality value location distribution, GC content, PCR duplication content, kmer frequency and so on. In the differential gene expression analysis, according to the obtained FPKM value, an internationally recognized algorithm EB Seq was adopted for differential screening. Here, when screening, LOG 2FC>1 or ←−1, FDR<0.05. In order to better understand the function of differentially expressed genes, we carried out Gene Ontology and signaling pathway analysis on differentially expressed genes, and carried out functional annotation and protein interaction network analysis on differentially expressed genes. In view of the above data analysis results, we screened the down-regulated differentially expressed genes SPAG7, ARHGAP11A or C16ORF7 in combination with literature.

Example 2 SPAG7, ARHGAP11A or C16ORF7 Gene Expression in Peripheral Blood of Patients with Senile Dementia and in Peripheral Blood of Healthy People I. Material and Method
1. Materials The peripheral blood of 95 patients with senile dementia and 31 healthy people were collected and divided into groups and numbered.

2. Method 2.1 Extraction of Total RNA from Peripheral Blood of Patients with Senile Dementia and Healthy People TRIzol® Reagent was used to extract sample RNA, and the experimental operation was carried out according to the product instructions, as shown in the instructions.

RNA quality criteria: the OD260/OD280 values of RNA samples were between 1.7 and 2.2. The total RNA electrophoretic patterns had clear 28S and 18S bands, and there was no significant difference between the electrophoretic patterns after heat preservation in water bath at 70° C. for 1 hour and before heat preservation in water bath.

2.2 Synthesis of cDNA by Reverse Transcription cDNA reverse transcription was carried out with SuperScript® III Reverse Transcriptase (Invitrogen, Cat. No. 18080-044). The experimental operation was carried out according to the product instruction. The specific operations were as follows:

with reverse transcription kit, using reverse transcription buffer to reverse transcribe 1 μg total RNA to synthesize cDNA. Adopting a 25 μl reaction system, taking 1 μg total RNA of each sample as template RNA, and respectively adding the following components into a PCR tube:

5× reverse transcription buffer 5 μl, 10 mmol/l dNTP 1.25 μl, 0.1 mmol/l DTT 2.5 μl, 30 μmmol/l OligodT 2 μl, 200 U/μl MMLV 1.25 template RNA 1 μg, adding sterile water to total system of 25 μl. Incubating at 42° C. for 1 hour, 72° C. for 10 minutes, and centrifuge for a short time. cDNA was stored in −20° C. refrigerator for later use.

2.3 Real-Time PCR 2.3.1 Instruments and Analytical Methods

The relative quantitative analysis of the data was carried out by using ABI 7500 fluorescence quantitative PCR instrument and 2-ΔΔCT method.

2.3.2 Primer Design

SPAG7 sequence NM_004890.2, ARHGAP11A sequence NM_001286479.2 or C16ORF7 sequence NM_004913.3 were designed with online primer design software, and synthesized by Invitrogen Corporation after primer design. The specific primer sequence is as follows:

TABLE 1

Primer sequences

| Gene | Number | Sequence | Length of amplification |
|---|---|---|---|
| SPAG7 | SEQ ID NO. 1 | gagaggagcatactacat | 81 bp |
|  | SEQ ID NO. 2 | atagcgacagtcatcatc |  |
| ARHGAP11A | SEQ ID NO. 3 | ttgctctcctgtcttctg | 114 bp |
|  | SEQ ID NO. 4 | gctgctgtccatcttattc |  |

TABLE 1-continued

Primer sequences

| Gene | Number | Sequence | Length of amplification |
|---|---|---|---|
| C16ORF7 | SEQ ID NO. 5 | atacacggaatacctgag | 75 bp |
|  | SEQ ID NO. 6 | gcttctttagtggtttcc |  |
| actin | SEQ ID NO. 7 | agttgcgttacaccctttcttg | 150 bp |
|  | SEQ ID NO. 8 | tcaccttcaccgttccagttt |  |

The operation process is as follows:
(1) reaction system: amplification was carried out with Power SYBR® Green PCR Master Mix (Invitrogen, Cat. No. 4367659) and the experimental operation was carried out according to the product specification. The amplification procedure is as follows: 95° 10 min, (95° C. 15 sec, 55° C. 60 sec)×35 cycles.

TABLE 2

RealTime Reaction System

| Component | Amount of addition |
|---|---|
| 2 x mix | 10 μl |
| Forward primer (10 μM) | 0.5 μl |
| Reverse primer (10 μM) | 0.5 μl |
| Template | 2 μl |
| Adding sterile distilled water | To 25 μl |

(2) Primer Screening

After the cDNA of each sample was mixed, the samples were diluted with 5 times gradient. 2 μl of the diluted samples were taken as templates and amplified with target gene primers and internal reference gene primers respectively. At the same time, the melting curve was analyzed at 60-95° C. The primers were screened according to the principle of high amplification efficiency and unimodal dissolution profile.

(3) Sample RealTime PCR Detection

After cDNA 10-fold dilution, 2 μl of each sample was used as template and amplified with target gene primer and internal reference gene primer respectively. Dissolution profile analysis was also performed at 60-95° C.

II. Experimental Results

The inflection point of the real-time quantitative PCR amplification curve is clear, and the overall parallelism of the amplification curve is good, indicating that the amplification efficiency of each reaction tube is similar; the limit is flat but not rising now, the slope of the exponential period of the curve is large, indicating that the amplification efficiency is high; and the dissolution profiles of sample amplification products are all single peak, indicating that there is only one amplification product, which is specific amplification. According to the relative quantitative formula of qRT-PCR: $2\text{-}\Delta Ct \times 100\%$, the expression levels of SPAG7, ARHGAP11A or C16ORF7 gene in the peripheral blood of patients with senile dementia and healthy people were compared. The results showed that (see FIG. 1): the results of qRT-PCR amplification were stable, in which the expression levels of SPAG7 and ARHGAP11A in the peripheral blood of patients with senile dementia were lower than those of healthy people, and the expression of SPAG7 was about ⅙ of that of the control group. Compared with the gene expression of the healthy group, 72 of 95 patients with disease had low expression of SPAG7, 7 of whom had no significant difference; the expression of ARHGAP11A was about ⅕ of that of the control group, 73 of 95 patients with disease had low expression of ARHGAP11A, and 9 of whom had no significant difference; and the expression level of C16ORF7 in peripheral blood of Alzheimer patients was 7 times higher than that of healthy controls, 72 of 95 patients with Alzheimer's disease had high expression of C16ORF7, and 9 of whom had no significant difference. The above results confirmed the results of integrated analysis of expression data in high throughput transcriptional group.

Example 3 Gene Silencing Experiment in Microglia

The researchers found that tau protein and α-Syn protein levels in living skin samples from patients with senile dementia or Parkinson's disease were significantly higher than those in the control group. In order to further verify the correlation between SPAG7, ARHGAP11A and senile dementia in this application, the inventor provided the SPAG7 and ARHGAP11A gene sequences to the biosynthesis company to design and synthesize interfering RNA, and fed back the synthesized products, in the meantime, providing unintentional interfering RNA as a control, silencing the expression of genes SPAG7 and ARHGAP11A in microglia respectively, and then detecting the expression of α-Syn. After the application found that SPAG7 and ARHGAP11A genes were silenced, the expression of α-Syn increased, and the expression of α-Syn protein increased more significantly in ARHGAP11A silence group. α-Syn protein was closely related to Alzheimer's disease, indicating that the two genes found in this application are not only closely related to Alzheimer's disease, but also can be further used as therapeutic targets for later drug research and development of Alzheimer's disease.

The invention adopts high-throughput sequencing to screen the related pathogenic gene SPAG7, ARHGAP11A or C16ORF7 of senile dementia, and verifies that SPAG7, ARHGAP11A or C16ORF7 play an important role in senile dementia by combining with molecular biology experiments. The invention provides a new target for clinical diagnosis and treatment of senile dementia, and has good clinical application prospect.

The invention claimed is:

1. A method of detecting the risk of a neurodegenerative disease in a subject, the method comprising a step of determining the expression level of ARHGAP11A or SPAG7 in a sample obtained from the subject and diagnosing the subject as having a high risk of neurodegenerative disease if the ARHGAP11A or SPAG7 expression level of the sample is below that of a control subject.

2. The method of claim 1, wherein the expression level of ARHGAP11A or SPAG7 is determined by fluorescence quantitative PCR, DNA microarray, or sequencing.

3. The method of claim 1, wherein the expression level of ARHGAP11A or SPAG7 is determined by an immunoassay.

* * * * *

SEQUENCE LISTING

<160> NUMBER OF SEQ ID NOS: 8

<210> SEQ ID NO 1
<211> LENGTH: 18
<212> TYPE: DNA

```
<213> ORGANISM: Artificial Sequence
<220> FEATURE:
<223> OTHER INFORMATION: SPAG7 F Primer

<400> SEQUENCE: 1
gagaggagca tactacat                                                 18

<210> SEQ ID NO 2
<211> LENGTH: 18
<212> TYPE: DNA
<213> ORGANISM: Artificial Sequence
<220> FEATURE:
<223> OTHER INFORMATION: SPAG7 R Primer

<400> SEQUENCE: 2
atagcgacag tcatcatc                                                 18

<210> SEQ ID NO 3
<211> LENGTH: 18
<212> TYPE: DNA
<213> ORGANISM: Artificial Sequence
<220> FEATURE:
<223> OTHER INFORMATION: ARHGAP11A F Primer

<400> SEQUENCE: 3
ttgctctcct gtcttctg                                                 18

<210> SEQ ID NO 4
<211> LENGTH: 19
<212> TYPE: DNA
<213> ORGANISM: Artificial Sequence
<220> FEATURE:
<223> OTHER INFORMATION: ARHGAP11A R Primer

<400> SEQUENCE: 4
gctgctgtcc atcttattc                                                19

<210> SEQ ID NO 5
<211> LENGTH: 18
<212> TYPE: DNA
<213> ORGANISM: Artificial Sequence
<220> FEATURE:
<223> OTHER INFORMATION: C16ORF7 F Primer

<400> SEQUENCE: 5
atacacggaa tacctgag                                                 18

<210> SEQ ID NO 6
<211> LENGTH: 18
<212> TYPE: DNA
<213> ORGANISM: Artificial Sequence
<220> FEATURE:
<223> OTHER INFORMATION: C16ORF7 R Primer

<400> SEQUENCE: 6
gcttctttag tggtttcc                                                 18

<210> SEQ ID NO 7
<211> LENGTH: 22
<212> TYPE: DNA
<213> ORGANISM: Artificial Sequence
<220> FEATURE:
<223> OTHER INFORMATION: Actin F Primer

<400> SEQUENCE: 7
agttgcgtta caccctttct tg                                            22
```

```
<210> SEQ ID NO 8
<211> LENGTH: 21
<212> TYPE: DNA
<213> ORGANISM: Artificial Sequence
<220> FEATURE:
<223> OTHER INFORMATION: Actin R Primer

<400> SEQUENCE: 8
tcaccttcac cgttccagtt t                                              21
```